United States Patent [19]

Wathen

[11] Patent Number: 5,284,764
[45] Date of Patent: Feb. 8, 1994

[54] CHIMERIC GLYCOPROTEINS CONTAINING IMMUNOGENIC SEGMENTS OF HUMAN PARAINFLUENZA VIRUS TYPE 3

[75] Inventor: Michael W. Wathen, Portage, Mich.

[73] Assignee: The Upjohn Company, Kalamazoo, Mich.

[21] Appl. No.: 941,027

[22] Filed: Sep. 4, 1992

Related U.S. Application Data

[60] Division of Ser. No. 582,891, Oct. 5, 1990, Pat. No. 5,169,628, which is a continuation of Ser. No. 184,648, Apr. 22, 1988, abandoned.

[51] Int. Cl.$^5$ .............. C12N 15/85; C12N 5/16; C12N 5/00
[52] U.S. Cl. .................. 435/240.2; 435/254.2; 435/320.1; 435/69.7; 435/172.3
[58] Field of Search .......... 435/240.2, 252.3, 252.33, 435/255, 320.1, 69.7, 172.3

[56] References Cited

U.S. PATENT DOCUMENTS 4,743,553 5/1988 Rice ............................ 435/253

FOREIGN PATENT DOCUMENTS 214555 3/1987 European Pat. Off. .

OTHER PUBLICATIONS

Spriggs (1988) J. Virol. 62, 1293–1296.
Ray et al (1988) J. Virol. 62, 783–787.
Ray et al. (1985) J. Infect. Dis. 152, 1219–1230.
Campo in "DNA Cloning Vol. II" (D. M. Gloren Ed.) IRL Press, Wash. DC pp. 213–238 (1986).
Luckow et al. (1988) Bio/Technology 6, 47–55.
Coleingh et al (1987) Virology 160, 465–472.
Elango et al (1986) J. Virol. 57, 481–489.
Spriggs et al. (1986) Virology 152, 241–251.
Thomsen et al (1984) Proc. Natl. Acad. Sci. 81, 659–663.

*Primary Examiner*—Keith Baker
*Attorney, Agent, or Firm*—Donald Corneglio; Mark DeLuca

[57] ABSTRACT

This invention encompasses novel chimeric glycoproteins which are useful for preparing virus specific immune responses against human parainfluenza virus type 3, PIV3. Host cells transformed with structural genes coding for the glycoproteins, expression and replication plasmids containing the structural genes, vaccines made from the glycoproteins and methods for protecting humans by inoculation with said vaccines are also part of this invention.

9 Claims, No Drawings

CHIMERIC GLYCOPROTEINS CONTAINING IMMUNOGENIC SEGMENTS OF HUMAN PARAINFLUENZA VIRUS TYPE 3

CROSS-REFERENCE TO RELATED PATENT APPLICATIONS

This application is a divisional of U.S. Ser. No. 07/582,891, filed Oct. 5, 1990, now U.S. Pat. No. 5,169,628, which was the U.S. National Phase application of PCT/US89/00814, filed Mar. 3, 1989, which was a continuation of U.S. Ser. No. 07/184,648, filed Apr. 22, 1988, abandoned.

FIELD OF THE INVENTION

This invention encompasses novel chimeric glycoproteins which are useful for preparing virus specific immune responses against human parainfluenza virus type 3, PIV3. Host cells transformed with structural genes coding for the glycoproteins, expression and replication plasmids containing the structural genes, vaccines made from the glycoproteins and methods for protecting humans by inoculation with said vaccines are also part of this invention.

BACKGROUND

Human parainfluenza virus type 3, PIV3, is an important primary cause of severe lower respiratory tract disease in infants and young children. The virus occurs worldwide and infects virtually all children under the age of four. Acute respiratory disease and secondary complications are particularly serious in infants and young children due to the immaturity of the respiratory system and may require hospitalization in severe cases. Lower respiratory infections are referable to all segments of the respiratory tract, are usually associated with fever, cough, runny nose, and fatigue, and are diagnosed clinically as bronchitis, bronchiolitis, pneumonia, croup, or viral infection. Older children and adults are also frequently reinfected although reinfection typically results in less severe upper respiratory tract illness.

Attempts to develop effective PIV3 vaccines have been largely unsuccessful. Clinical studies using live or inactivated PIV3 vaccines demonstrated an increase in virus specific serum antibodies but provided no significant protection against the disease.

INFORMATION DISCLOSURE STATEMENT

The recombinant vaccinia virus expression system is known to separately express the F and HN glycoproteins of PIV3 and to separately induce protective immune responses in challenged cotton rats, Collins, P. L., et al, Expression of the F and HN Glycoproteins of Human Parainfluenza Virus Type 3 by Recombinant Vaccinia Viruses: Contributions of the Individual Proteins to Host Immunity, Journal of Virology 61: 3416–3423 (1987). The recombinant vaccinia virus expression system is also known to induce PIV3-specific serum neutralizing antibodies and to confer resistance to PIV3 replication in the respiratory tract in primates, Collins, P. L., et al., Journal of Virology 62: 1293–1296 (1988). Immunization with a mixture of purified F and HN glycoproteins induced virus neutralizing activity and afforded complete protection from challenge infection in hamsters, Ray, R., et al., Journal of Virology 62: 783–787 (1988).

SUMMARY OF THE INVENTION

This invention encompasses a polypeptide comprising a signal sequence and at least one immunogenic fragment from both human parainfluenza virus type 3 glycoproteins F and HN. The use of this protein as a vaccine, methods to prevent PIV3-related disease and preparation of this protein using recombinant techniques are also part of this invention.

DETAILED DESCRIPTION

The following defined terms are used in this specification. The phrase "cell culture" refers to the containment of growing cells derived from either a multicellular plant or animal which allows for the cells to remain viable outside the original plant or animal. The term "downstream" identifies sequences proceeding farther in the direction of expression; for example, the coding region is downstream from the initiation codon. The term "upstream" identifies sequences proceeding in the opposite direction from expression; for example, the bacterial promoter is upstream from the transcription unit, the initiation codon is upstream from the coding region. The term "microorganism" includes both single cellular prokaryote and eukaryote organisms such as bacteria, actinomycetes and yeast. The term "operon" is a complete unit of gene expression and regulation, including structural genes, regulator genes and control elements in DNA recognized by regulator gene product. The term "plasmid" refers to an autonomous self-replicating extrachromosomal circular DNA and includes both the expression and nonexpression types. Where a recombinant microorganism or cell culture is described as hosting an expression plasmid the phrase "expression plasmid" includes both extrachromosomal circular DNA and DNA that has been incorporated into the host chromosome(s). Where a plasmid is being maintained by a host cell, the plasmid is either being stably replicated by the cells during mitosis as an autonomous structure or as an incorporated portion of the host's genome. The term "promoter" is a region of DNA involved in binding the RNA polymerase to initiate transcription. The phrase "DNA sequence" refers to a single or double stranded DNA molecule comprised of nucleotide bases, adenosine, thymidine, cytosine and guanosine. The phrase "essentially pure" refers to a composition of protein that contains no parainfluenza virus protein other than the desired recombinant chimeric glycoprotein. Although the essentially pure proteins may be contaminated with low levels of host cell constituents, the protein is devoid of contaminating structural and non-structural viral protein produced by replicating parainfluenza viruses. The phrase "suitable host" refers to a cell culture or microorganism that is compatible with a recombinant plasmid and will permit the plasmid to replicate, to be incorporated into its genome or to be expressed.

This invention involves a series of molecular genetic manipulations that can be achieved in a variety of known ways. The manipulations can be summarized as obtaining a cDNA of the protein, the cloning and replication of the cDNA in E. coli and the expression of the desired cDNA in a suitable host. The following descriptions will detail the various methods available to express the protein and are followed by specific examples of preferred methods.

Generally, the nomenclature and general laboratory procedures required in this invention can be found in Maniatis, et al., Molecular Cloning A Laboratory Manual, Cold Spring Harbor Laboratory, Cold Spring Harbor, N.Y. (1982).

All E. coli strains are grown on Luria broth (LB) with glucose, Difco's Antibiotic Medium #2 and M9 medium supplemented with glucose and acid-hydrolyzed casein amino acids. Strains with resistance to antibiotics were maintained at the drug concentrations described in Maniatis. Transformations were performed according to the method described by Rowekamp and Firtel, Dev. Biol., 79:409–418 (1980).

All enzymes were used according to the manufacturer's instructions. Transformants were analyzed by colony hybridization as described in Grunstein and Wallis, Methods in Enzymology, 68:379–388.

After hybridization, the probes are removed and saved, and the filters are washed in 0.1% SDS, 0.2x SSC for a total of 3 hours with 5 changes of 400 ml each. Filters are thoroughly air dried, mounted, and autoradiographed using Kodak X-OMAT AR film and Dupont Cronex Lightening Plus intensifying screens for an appropriate time at −70° C.

For sequencing of plasmids, purified plasmid DNA is prepared according to the methods described in Maniatis. End-labeled DNA fragments are prepared and analyzed by the chemical sequencing methods of Maxam and Gilbert with modifications described by Collins and Wertz, J. Virol. 54:65–71 (1985).

Nucleotide sizes are given in either kilobases (Kb) or basepairs (bp). These are estimates derived from agarose gel electrophoresis.

The first step in obtaining expression of protein is to obtain the DNA sequence coding for the protein from cDNA clones. This sequence is then cloned into an expression plasmid which is capable of directing transcription of the gene and allowing efficient translation of the transcript. The library method for obtaining cDNA encoding proteins is described generally in Maniatis, and specifically by Elango, et al., in Human Parainfluenza Type 3 Virus Hemagglutinin-Neuraminidase Glycoprotein: Nucleotide sequence of mRNA and Limited Amino Acid Sequence of the Purified Protein, J. Virol. 57: 481–489 (1986) and by Spriggs, et al., in Fusion Glycoprotein of Human Parainfluenza Virus Type 3: Nucleotide Sequence of the Gene, Direct Identification of the Cleavage-Activation Site, and Comparison with Other Paramyxoviruses, Virology 152: 241–251 (1986).

Clones are prepared by inserting the cDNA into PstI cleaved pBR322 to which homopolymer tracts of dGTP have been enzymatically added to the 3' ends at the cleavage site. Homopolymer tracts of dCTP are enzymatically added to the 3' termini of the cDNA molecules according to the methods described by Maniatis. Ideally, 10–30 residues of dCTP or dGTP should be added to maximize cloning efficiency. The cDNA and plasmid are annealed together and transformed into E. coli. The clones containing full length cDNA are detected by probes of labeled viral cDNA or oligonucleotides complementary to portions of the gene sequences, followed by restriction enzyme analysis and DNA sequencing.

Oligonucleotides are chemically synthesized according to the solid phase phosphoramidite triester method first described by Beaucage and Caruthers, Tetrahedron Letters, 22(20):1859–1862 (1981) using an automated synthesizer, as described in Needham-VanDevanter, et al., Nucleic Acids Res., 12:6159–6168 (1984).

Purification of oligonucleotides is by either native acrylamide gel electrophoresis or by anion-exchange HPLC as described in Pearson and Regnier, J. Chrom., 255:137–149 (1983).

The sequence of the synthetic oligonucleotides can be verified using the chemical degradation method of Maxam and Gilbert, Grossman and Moldave, eds., Academic Press, New York, Methods in Enzymology, 65:499–560 (1980).

To obtain high level expression of a cloned gene in a prokaryotic system, it is essential to construct expression vectors which contain, at the minimum, a strong promoter to direct mRNA transcription, a ribosome binding site for translational initiation, and a transcription terminator. Examples of regulatory regions suitable for this purpose are the promoter and operator region of the E. coli tryptophan biosynthetic pathway as described by Yanofsky, Kelley, and Horn, J. Bacteriol., 158:1018–1024 (1984) and the leftward promoter of phage lambda ($P_L$) as described by Herskowitz and Hagen, Ann. Rev. Genet., 14:399–445 (1980).

The proteins produced in E. coli will not fold properly due to the presence of cysteine residues and to the lack of suitable post-translational modifications. During purification from E. coli, the expressed proteins must first be denatured and then renatured. This can be accomplished by solubilizing the E. coli produced proteins in guanidine HCl and reducing all the cysteine residues with β-mercaptoethanol. The protein is then renatured either by slow dialysis or by gel filtration, U.S. Pat. No. 4,511,503.

Detection of proteins is achieved by methods known in the art such as radioimmunoassays, or Western blotting techniques or immunoprecipitation. Purification from E. coli can be achieved following procedures described in U.S. Pat. No. 4,511,503.

Expression of heterologous proteins in yeast is well known and described. Methods in Yeast Genetics, Sherman, et al., Cold Spring Harbor Laboratory, (1982) is a well recognized work describing the various methods used to produce proteins in yeast.

For high level expression of a gene in yeast, it is essential to connect the gene to a strong promoter system as in the prokaryote and to also provide efficient transcription termination/polyadenylation sequences from a yeast gene. Examples of useful promoters include GAL1,10, Johnston and Davis, Mol. and Cell. Biol., 4:1440–1448, 1984), ADH2, Russell, et al., J. Biol. Chem. 258:2674–2682, 1983), PHO5, EMBOJ. 6:675–680, (1982), and MFα1. A multicopy plasmid with a selective marker such as Lue-2, URA-3, Trp-1, or His-3 is also desirable. The MFα1 promoter is preferred. The MFα1 promoter, in a host of the α mating-type is constitutive, but is off in diploids or cells with the a mating-type. It can, however, be regulated by raising or lowering temperature in hosts which have a ts mutation at one of the SIR loci. The effect of such a mutation at 35° C. on an α type cell is to turn on the normally silent gene coding for the a mating-type. The expression of the silent a mating-type gene, in turn, turns off the MFα1 promoter. Lowering the temperature of growth to 27° C. reverses the whole process, i.e., turns the a mating-type off and turns the MFα1 on, Herskowitz and Oshima, The Molecular Biology of the Yeast Saccharomyces, Strathern, Jones, and Broach, eds., Cold Spring Harbor Lab., Cold Spring Harbor, N.Y., 181–209, (1982).

The polyadenylation sequences are provided by the 3'-end sequences of any of the highly expressed genes, like ADH1, MFα1, or TPI, Alber and Kawasaki, J. of Mol. and Appl. Genet. 1:419-434, (1982).

A number of yeast expression plasmids like YEp6, YEp13, YEp24 can be used as vectors. A gene of interest can be fused to any of the promoters mentioned above, and then ligated to the plasmids for expression in various yeast hosts. These plasmids have been fully described in the literature, Botstein, et al., Gene, 8:17-24, (1979); Broach, et al., Gene, 8:121-133, (1979).

Two procedures are used in transforming yeast cells. In one case, yeast cells are first converted into protoplasts using zymolyase, lyticase or glusulase, followed by addition of DNA and polyethylene glycol (PEG). The PEG-treated protoplasts are then regenerated in a 3% agar medium under selective conditions. Details of this procedure are given in the papers by Beggs, Nature (London), 275:104-109 (1978); and Hinnen, et al., Proc. Natl. Acad. Sci. USA, 75:1929-1933 (1978). The second procedure does not involve removal of the cell wall. Instead the cells are treated with lithium-chloride or acetate and PEG and put on selective plates, Ito, et al., J. Bact., 153:163-168, (1983).

The cDNA can be ligated to various expression vectors for use in transforming host cell cultures. The vectors all contain gene sequences to initiate transcription and translation of the proteins that are compatible with the host cell to be transformed.

In addition, the vectors preferably contain a marker to provide a phenotypic trait for selection of transformed host cells such as dihydrofolate reductase or metallothionein. Additionally a replicating vector might contain a replicon.

Insect or mammalian cell cultures are useful for the production of proteins. Mammalian cell systems often will be in the form of monolayers of cells although mammalian cell suspensions may also be used. Illustrative examples of mammalian cell lines include VERO and HeLa cells, Chinese hamster ovary (CHO) cell lines, WI38, BHK, COS-7 or MDCK cell lines.

The vector which is used to transform the host cell preferably contains gene sequences to initiate the transcription and translation of the protein's gene sequence. These sequences are referred to as expression control sequences. When the host cell is of mammalian or insect origin illustrative useful expression control sequences are obtained from the SV-40 promoter, Science, 222, 524-527 (1983), the CMV I.E. promoter, Proc. Natl. Acad. Sci. 81:659-663 (1984), the metallothionein promoter, Nature, 296, 39-42, (1982) or the baculovirus polyhedrin promoter (insect cells), Virol., 131, 561-565 (1983). The plasmid for replicating or integrating DNA material containing the expression control sequences is cleaved using restriction enzymes and adjusted in size as necessary or desirable an(i ligated with cDNA coding for proteins using methods well known in the art.

When higher animal host cells are employed, polyadenylation or transcription terminator sequences from known mammalian genes need to be incorporated into the vector. An example of a terminator sequence is the polyadenylation sequence from the bovine growth hormone gene. Additionally gene sequences to control replication in the host cell may be incorporated into the vector such as those found in bovine papillomavirus type-vectors, Saveria-Campo, "Bovine papillomavirus DNA: a eukaryotic cloning vector", DNA Cloning Vol. II—A practical approach, Glover, ed., IRL Press, Arlington, Va. 213-238 (1985).

The preferred expression vector useful for expressing proteins in Chinese hamster ovary (CHO) cells is a shuttle vector pSVCOW7 which replicates in both CHO and E. coli cells utilizing ampicillin resistance and dihydrofolate reductase genes as markers in E. coli and CHO cells respectively. Plasmid pSVCOW7 also provides the polyadenylation sequence from bovine growth hormone which is necessary for expression in CHO cells. Plasmid pSVCOW7 is cleaved and a viral promoter and cDNAs inserted.

The preferred expression vector useful in forming recombinant baculovirus for expressing proteins in insect cells is pAc373, Smith, et al., Mol. Cell. Biol. 3:2156-2165 (1983). The plasmid replicates in E. coli cells utilizing ampicillin resistance, and provides the eukaryotic promoter and polyadenylation signal from the baculovirus polyhedrin gene for expression of genes. Plasmid pAc373 is cleaved and a cDNA is inserted adjacent to the promoter. This new plasmid is cotransfected with baculovirus (Autograpa californica nuclear polyhedrosis virus) DNA into insect cells by calcium phosphate precipitation. Recombinant baculovirus in which the pAc373 polyhedrin gene containing a cDNA has replaced the resident viral polyhedrin gene by homologous recombination is detected by dot blot hybridization using $^{32}P$-labeled cDNA as a probe, Summers and Smith, A Manual of Methods for Baculovirus Vectors and Insect Cell Culture Procedures, Texas A & M University, College Station, Tex., 29-30 (1986). Insect cells infected with recombinant baculovirus may also be differentiated by their occlusion-negative morphology since the insertion of the cDNA into the polyhedrin gene prevents the synthesis of this occlusion-forming protein.

The preferred expression vector used in conjunction with bovine papilloma virus (BPV) for expressing proteins is pTFW9 (Plasmid pTWF9 was deposited in accordance with the Budapest Treaty. Plasmid pTFW9 is maintained in an E. coli host and has been deposited with the Northern Regional Research Center, Peoria, Ill., U.S.A. on Nov. 17, 1986 and assigned Accession Number NRRL B-18141.) The plasmid replicates in E. coli utilizing ampicillin resistance, and provides the mouse metallothionein promoter and SV40 polyadenylation signal for expression of genes. Plasmid pTFW9 is cleaved and a cDNA is inserted adjacent to the promoter. This new plasmid is then cleaved to allow insertion of BPV. The recombinant plasmid is transfected into animal cells by calcium phosphate precipitation and foci of transformed cells are selected.

The host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, and microinjection of the DNA directly into the cells. The transfected cells are cultured by means well known in the art, Biochemical Methods in Cell Culture and Virology, Kuchier, Dowden, Hutchinson and Ross, Inc., (1977). Recombinant glycoproteins expressed in one of the above eukaryotic expression systems are isolated from cell suspensions created by disruption of the host cell system by well known mechanical or enzymatic means. Proteins which are designed to be secreted from the cells are isolated from the media without disruption of the cells. For purification of glycoproteins it is helpful to first apply the cytoplasmic fraction to a lentil lectin column which will specifically bind glycoproteins. The eluted glycoproteins are then applied to an affinity column containing antibody.

A typical glycoprotein can be divided into three regions. At the amino terminal end is a hydrophobic region called the signal sequence. This sequence of amino acids signals the transport of the glycoprotein to the cell membrane. Following transport the signal sequence is removed by cleavage. Downstream from the signal sequence is the extracellular domain of the mature glycoprotein. This is the immunogenic portion of the glycoprotein since it is accessible to antibodies. At the carboxy terminal end of the glycoprotein is the hydrophobic anchor region which causes the glycoprotein to be retained in the cell membrane. The PIV3 F is a typical glycoprotein in that it contains an amino terminal signal sequence and carboxy terminal anchor sequence, Spriggs, et al., Virology 152:241-25, (1986). However, the PIV3 HN glycoprotein is unusual since its amino terminal end acts as both a signal and anchor region, Elango, et al., J. Virol. 57:481-489, (1986).

A glycoprotein may be designed to be secreted from cells into the surrounding media. This is accomplished by causing the early termination of the glycoprotein before translation of the anchor region, Lasky, et al., Biotechnology, 2:527-532 (1984). Early termination may be accomplished by inserting a universal translational terminator oligonucleotide into an appropriate site in the gene's DNA. These oligonucleotides are commercially available. Early termination may also be accomplished by altering the reading frame, thus generating a translational termination codon.

The chimeric glycoprotein described below consists of the signal and extracellular domains of PIV3 F linked to the extracellular domain of PIV3 HN, and will be referred to as FHN. When properly placed in a eukaryotic expression vector, the FHN gene described above is designed to express a chimeric glycoprotein which would be transported to the cell's surface and secreted into the media.

The majority of the cytoplasmic domain of the PIV3 HN protein is contained within the coding region spanned by the DraI (nucleotide position 452 of the protein coding region) and PstI (nucleotide position 1709 of the protein coding region) restriction enzyme sites. This sequence does not code for the signal/anchor region of the glycoprotein. The majority of the cytoplasmic domain of the PIV3 F protein is contained within the coding region prior to the XbaI (nucleotide position 1398 of the protein coding region) restriction enzyme site. This sequence codes for the signal region and the majority of the antigenic region, but not the anchor region of the F glycoprotein.

To insert the HN glycoprotein sequence into the F glycoprotein of PIV3, the HN gene is digested with PstI and the end is made blunt with T4 DNA polymerase. An XbaI linker (New England Biolabs) with the sequence

CTAGTCTAGACTAG
CATCAGATCTGATC is ligated to the end. The gene is separated from residual linker by agarose gel electrophoresis. The above linker contains an in phase translation termination signal to stop protein synthesis. The HN gene is then digested with DraI and a XbaI linker (New England Biolabs) with the sequence

TGCTCTAGAGCA
ACGAGATCTCGT is ligated to the end. This linker does not contain an in phase translation termination signal and will allow read through of the protein from the F to the HN sequences. The HN gene fragment (1.3 Kb) containing the linkers is digested with XbaI and separated from residual linkers by agarose gel electrophoresis. The PIV3 F gene is digested with XbaI and dephosphorylated with bacterial alkaline phosphatase. The 1.3 Kb HN fragment is then ligated into the F gene at the XbaI site and transformed into E. coli HB101. A clone containing the chimeric glycoprotein gene is isolated and the junctions between the F and HN DNA sequences are verified correct by Maxam-Gilbert sequencing. The PIV3 chimeric glycoprotein gene can be placed in an appropriate expression vector.

The above restriction enzyme sites were chosen because they allow for the expression of a large proportion of the relevant regions of the F and HN glycoproteins. However, other portions of the glycoproteins could be expressed by choosing other restriction enzyme sites within the F and HN coding sequences for the fusion of these genes. For instance, the restriction enzymes HaeIII, KpnI, or NlaIV could be used to cleave at the 5' end of the HN gene. The restriction enzymes BalI, BglII, or HaeIII could be used to cleave at the 3' end of the HN gene. The enzymes could be used in any combination of two with one enzyme being from each group to give immunogenic protein fragments. For the gpF gene, the BglII, HaeIII, NsiI, or XhoII restriction enzymes could be used in place of XbaI. Linker oligonucleotides could be added to correct the reading frame in the junction regions. Two oligonucleotides which would correct the two possible frame shifts are the SalI linkers GGTCGACC and CGGTCGACCG
CCAGCTGG      GCCAGCTGGC which are commercially available. Also when an anchor region is desired in the glycoprotein, a linker oligonucleotide is added a the second junction to allow synthesis of the gpF anchor region. Alternative strategies could be designed for the expression of a FHN chimeric protein by insertion or deletion of various sequences. The major criterion for the protein is the retention of a signal sequence and the immunologically important regions of the two glycoproteins.

Insertion of FHN gene into CHO, BPV, or baculovirus expression vectors is as already described.

The FHN chimeric glycoprotein offers advantages over expression of the individual glycoproteins. Since FHN is a single protein, it requires half the labor and reagents for purification compared to the separate F and HN glycoproteins. Also, the FHN chimeric glycoprotein is secreted into the media for ease of purification. The F glycoprotein can be engineered as a secreted glycoprotein by truncation prior to the anchor region sequences. However, the PIV3 HN glycoprotein contains a signal/anchor region at its amino terminal end. Therefore, truncation of this glycoprotein will not generate a secreted form. The signal/anchor region could be replaced with a signal region from a foreign glycoprotein, but this would introduce foreign protein sequences into the potential vaccine.

Conventions used to represent plasmids and fragments in Charts 1-6, are meant to be synonymous with conventional circular representations of plasmids and their fragments. Unlike the circular figures, the single line figures on the charts represent both circular and linear double-stranded DNA with initiation or transcription occurring from left to right (5' to 3'). Asterisks (*) represent the bridging of nucleotides to complete the circular form of the plasmids. Fragments do not have asterisk marks because they are linear pieces of double-stranded DNA. Endonuclease restriction sites are indicated above the line. Gene markers are indicated below the line. The relative spacing between markers do not indicate actual distances but are only meant to indicate their relative positions on the illustrated DNA sequence.

Example 1 Removing the G-C tails from the F glycoprotein gene—Chart 1

In order to obtain maximum expression of the F glycoprotein, the G-C nucleotides which are used to insert the cDNA into the plasmid pBR322 must be removed from the ends of the cDNA. In order to conveniently insert the FHN cDNA into the preferred expression vector for CHO cells (pSVCOW7, described below), or the preferred expression vector for baculovirus (pAc373, described below), it is necessary to supply a BamHI site upstream from the protein coding sequence. Methods for the synthesis of the cDNA clones containing the entire sequence for the F glycoprotein have been described. Spriggs, et al., Virology 152: 241-251, (1986).

The cDNA containing the intact PIV3 F gene (pGPF1) is digested with BstXI and NdeI. BstXI cleaves the F gene at position 39 relative to the gene's initiation codon, and NdeI cleaves at position 1599. Oligonucleotide I is ligated to the BstXI cleavage site and oligonucleotide 2 is ligated to the NdeI cleavage site. Oligonucleotide I contains the DNA sequences from 10 bases prior to the coding region to the BstXI cleavage site in the coding region of the F gene (−10 to +39), and has a BamHI site on the 5' end of the oligonucleotide. Oligonucleotide 2 contains the DNA sequences from the NdeI cleavage site to the termination codon of the F gene (+1599 to +1620). At the 3' end of oligonucleotide 2 is a NruI restriction enzyme site followed by a BamHI restriction enzyme site.

Following ligation of the oligonucleotides, the DNA is digested with BamHI and the F gene (fragment 1, 1.6 Kb) is gel purified. Fragment I is ligated into plasmid pBR322 (Pharmacia) which has been digested with BamHI and dephosphorylated with bacterial alkaline phosphatase. The plasmid (pGPF2) is transformed into E. coli HB101. The newly synthesized regions of pGPF2 are sequenced by the Maxam-Gilbert procedure to verify accurate synthesis and ligation.

Example 2 Construction of a PIV3 Chimeric FHN Gene—Chart 2

A. Preparation of the PIV3 HN glycoprotein gene. Clones containing the entire coding region of the PIV3 HN gene and methods for isolating such clones have been described. Elango, et al., J. Virol. 57:481-489, (1986). A cDNA clone containing the PIV3 HN gene (pGPHN1) is digested with PstI. This enzyme cleaves toward the 3' end of the HN gene (nucleotide +1714). The ends of the fragment are made blunt with T4 DNA polymerase and then dephosphorylated with bacterial alkaline phosphatase. An XbaI linker (New England Biolabs; linker 1) with the sequence

CTAGTCTAGACTAG
GATCAGATCTGATC is ligated to the end. The cDNA is separated from residual linker by electrophoresis in a 1.2% agarose gel. The 1.7 Kb fragment (fragment 2) containing the HN gene is excised from the gel and the DNA is purified from the agarose. The above linker contains an in phase translation termination signal to stop protein synthesis. The HN gene is then digested with DraI. This enzyme cleaves 3' to the signal/anchor encoding region of the HN gene (nucleotide +452). A XbaI linker (New England Biolabs; linker 2) with the sequence

TGCTCTAGAGCA
ACGAGATCTCGT is ligated to the end. This linker does not contain an in phase translation termination signal. The DNA is digested with XbaI and separated from residual linkers by electrophoresis in a 1.2% agarose gel. The 1.3 Kb fragment containing the relevant region of the HN gene is excised from the gel and the DNA is purified from the agarose.

B. Insertion of the HN cDNA into the PIV3 F glycoprotein gene.

Plasmid pGPF2 is digested with XbaI and dephosphorylated with bacterial alkaline phosphatase. The 1.3 Kb fragment is ligated into the XbaI site to yield the chimeric FHN gene (pGPFHN1). The plasmid is transformed into E. coli HB101. Clones are isolated and selected from the correct orientation of the HN cDNA within the F gene by digestion with BamHI and PvuII which will generate fragments of approximately 2.5 Kb and 350 bp within the FHN gene. The incorrect orientation of the HN fragment will yield fragments of approximately 1.5 Kb and 1.3 Kb upon digestion with BamHI and PvuII. The junction regions of a properly orientated clone are sequenced by the Maxam-Gilbert technique to verify proper ligation of the HN fragment.

Oligonucleotide 1
CGGATCCACTGAACATGATGCAACCTCAATACTGCTAATTATTACAACCATGATT
GCCTAGGTGACTTGTACTACGTTGGAGTTATGACGATTAATAATGTTGGTA Oligonucleotide 2
TATGTATTAACAAACAAATGATCGCGACGGATCCG
ACATAATTGTTTGTTTACTAGCGCTGCCTAGGC

Example 3 Using DNA oligonucleotides to generate genes coding for chimeric FHN glycoproteins of various lengths—Chart 3

Genes coding for chimeric FHN glycoproteins containing various regions of the F and HN glycoproteins can be generated using a combination of restriction enzymes and oligonucleotides. This procedure allows the F and HN glycoproteins to be linked at any desirable point of their amino acid backbone, permitting incorporation or removal of regions likely to contain epitopes which will be recognized by the host immune system. Individual amino acids may also be changed if so desired. Oligonucleotides are synthesized corresponding to the DNA sequence from the point of desired linkage to a convenient restriction enzyme site. The glycoprotein gene is digested with that restriction enzyme and the oligonucleotide is ligated to the gene at the restriction enzyme site to generate a DNA fragment of the desired length. The oligonucleotides are synthesized with ends compatible with the restriction enzyme sites for ease of ligation.

A. Insertion of Glycoprotein HN cDNA into the F Glycoprotein Gene.

Clone pGPHN1 is digested with PstI and DraI. The 1.3 Kb fragment representing the cDNA region from nucleotide position 452 to 1714 (fragment 4) is gel purified. Oligonucleotides representing adjoining regions of the HN cDNA are then ligated to each end of fragment 4. The DNA sequences in these oligonucleotides may enclose nucleotides which would be included only in the terminal oligonucleotide. For instance, the enclosed nucleotides would not be included on oligonucleotide 5 if oligonucleotide 6 were to be added. These enclosed nucleotides code for a XbaI site. The enclosed nucleotides are not included when an additional oligonucleotide(s) is to be added in order to allow ligation between the compatible ends of the oligonucleotides. For instance, the 5' end of the oligonucleotide 3 is compatible with the 3' end of oligonucleotide 4 when the nucleotides enclosed by parentheses are not included in oligonucleotide 3. Oligonucleotide 8 is ligated to the 3' end of the HN gene fragment. The 5' end of this oligonucleotide is compatible with the 3' end of fragment 4. The 3' end of this oligonucleotide contains an in phase translation termination signal followed by a XbaI restriction enzyme site.

Following ligation of the oligonucleotides to the HN cDNA fragment, the DNA is digested with XbaI and the enlarged HN cDNA fragment (fragment 5) is gel purified. The new HN cDNA fragment is then ligated into XbaI digested pGPF2. The DNA is transformed into *E. coil* HB101 and a clone containing the HN gene in the correct orientation within the F gene is isolated (pGPFHN2). Orientation is determined by digestion with appropriate restriction enzymes. The newly synthesized regions of the chimeric gene are verified correct by Maxam-Gilbert sequencing. The clone may then be placed in various expression vectors as described below.

B. Oligonucleotides 3) (GTCTAGA AATTAGGA)ATGATAATCAAGAAGTGCCTCCACAAAGAATAA
(CAGATCT)TTAATCCT TACTATTAGTTCTTCACGGAGGTGTTTCTTATT

CACATGATGTGGGCATAAAACCTT
GTGTACTACACCCGTATTTTGGAA 4) (GTCTAGA
TATACCGA)TATCATTGACACAACAAATGTCGGATCTTAGGAAATT
(CAGATCT)ATATGGCT ATAGTAACTGTGTTGTTTACAGCCTAGAATCCTTTAA

CATTAGTGAAATTACAATTAGGA
GTAATCACTTTAATG 5) (GTCTAGA TCTAATAC)AGTCAGGAGTGAATACAAGGCTTCTTACAATTCAG
(CAGATCT)AGATTATG TCAGTCCTCACTTATGTTCCGAAGAATGTTAAGTC
AGTCATGTCCAGAATTATATACCGA
TCAGTACAGGTCTTAAT 6) (GTCTAGA CAATGAGT)TTATGGAAGTTACAGAAAAGATCCAAATGGCATCGG
(CAGATCT)GTTACTCA AATACCTTCAATGTCTTTTCTAGGTTTACCGTAGCC

ATAATATTAATGATCTAATAC
TATTATAATTACT

7) GTCTAGATTCCATCAAAAGTGAAAAAGCCCATGAATCATTGCTACAA
CAGATCTAAGGTAGTTTTCACTTTTTCGGGTACTTAGTAACGATGTT

GACGTAAACAATGAGT
CTGCATTT

8) GTTAATCTAGAG
ACGTCAATTAGATCTC code for additional epitopes found on the HN glycoprotein. The individual oligonucleotides were designed to incorporate regions which may contain unique epitopes. The oligonucleotide ligated to the 5' end of the HN cDNA may consist of either oligonucleotide 3 (cDNA nucleotides 395 to 452), oligonucleotides 3-4 (cDNA nucleotides 335 to 452), oligonucleotides 3-4-5 (cDNA nucleotides 275 to 452), oligonucleotides 3-4-5-6 (cDNA nucleotides 218 to 452), or oligonucleotides 3-4-5-6-7 (cDNA nucleotides 162 to 452). Parentheses

Example 4 Construction of a PIV3 chimeric FHN glycoprotein gene containing an anchor region—Chart 4

Examples 2 and 3 illustrate the synthesis of genes coding for chimeric FHN glycoproteins which do not contain anchor regions and will therefore be secreted into the medium of expressing cells. A gene coding for a chimeric FHN glycoprotein containing an anchor region can be synthesized. The anchor region would cause the retention of the chimeric glycoprotein in the cellular membranes in a manner similar to most viral glycoproteins. The anchor region may be on the carboxy-terminal end of the glycoprotein so that the immunogenic regions of the chimeric molecule from both the F and HN glycoproteins would protrude into the extracellular fluid. The gene described below will code for a chimeric glycoprotein consisting of the extracellular region of PIV3 F, the extracellular region of PIV3 HN, and the anchor region of PIV3 F in the above order from amino-terminus to carboxy-terminus.

A. Insertion of the HN cDNA fragment into the PIV3 F glycoprotein gene.

The clone pGPHN1 is digested with DraI and PstI. Oligonucleotide 9 is first ligated to the DNA fragment (oligonucleotide is compatible with DraI site). Oligonucleotide 10 is then ligated to the DNA fragment (compatible with PstI site). Both oligonucleotides contain XbaI restriction enzyme sites.

9) TGCTCTAGAGCA
   ACGAGATCTCGT

10) GTCTAGAG
    ACGTCAGATCTC

Following ligation, the DNA is digested with XbaI and the 1.3 Kb fragment of the HN cDNA (fragment 6) is gel purified. Fragment 6 is then ligated into XbaI digested pGPF2. The DNA is transformed into *E. coli* HB101. Clones are isolated and selected from the correct orientation as described in Example 2. The junction regions of a properly orientated clone are then verified correct by Maxam-Gilbert sequencing. This clone (pGPFHN3) may be placed in various expression vectors as described below.

Example 5 Construction of a PIV3 chimeric HNF glycoprotein gene

A portion of the extracellular region of the PIV3 F glycoprotein may be placed at the carboxy-terminal end of the HN glycoprotein. This chimeric glycoprotein would consist of the signal/anchor region from the amino-terminus of HN, the majority of the extracellular region of HN, and a portion of the extracellular region of F in the above order from amino-terminus to carboxy-terminus.

A. Preparation of the PIV3 HN glycoprotein gene—Chart 5.

To prepare clone pGPHN1 for expression, the G-C tails used in cDNA cloning must be removed and compatible restriction enzyme sites placed on its ends. Clone pGPHN1 is digested with HhpI. HphI cleaves at position 75 on the cDNA gene coding sequence. The following oligonucleotide is then ligated to the cDNA fragment:

tide 11, the DNA is digested with BamHI and PstI (PstI cleaves at nucleotide position 1714 in the HN gene). The DNA is electrophoresed in a 1.2% agarose gel. The 1.7 Kb HN cDNA fragment (fragment 7) is excised from the gel and the DNA is purified from the agarose. Fragment 7 is then ligated into pUC19 which has been digested with BamHI and PstI to yield pGPHN2. The plasmid is transformed into *E. coli* HB101 and plasmid DNA is isolated.

B. Insertion of an F cDNA fragment into the PIV3 HN glycoprotein gene—Chart 6.

The clone pGPF1 is digested with BstEII and XbaI. BstEII cleaves at position 190 and XbaI at position 1398 on the F cDNA gene sequence. The following oligonucleotides are then ligated to the cDNA fragment.

12) CCTGCAGGTG
    GGACGTCCACCACTG

13) CTAGAATAATAGTCGCGAGGATCCTGCAGG
    TTATTATCAGCGCTCCTAGGACGTCC

Oligonucleotide 12 will ligate to the BstEII site and will generate a PstI restriction enzyme site on the 5' end of the cDNA fragment. Oligonucleotide 13 will ligate to the XbaI site and will generate a translational termination codon, a NruI restriction enzyme site, a BamHI restriction enzyme site, and a PstI restriction enzyme site in the indicated order (5' to 3') on the 3' end of the cDNA fragment. The DNA is then digested with PstI and the 1.2 Kb F cDNA fragment (fragment 8) is gel purified. Fragment 8 is then ligated into pGPHN2 which has been digested with PstI. The plasmid is transformed into *E. coli* HB101. Clones are isolated and selected from the correct orientation of the F cDNA within the HN gene by digestion with BamHI and NruI which will generate a 2.9 Kb fragment. The incorrect orientation will generate a 1.7 Kb fragment. The junction regions of a properly orientated clone are then verified correct by Maxam-Gilbert sequencing. This clone (pGPHNF1) may be placed in various expression vectors as described below.

Example 6 Expression of the Chimeric FHN Glycoprotein of PIV3 in CHO Cells

A. Construction of pSVCOW7

The starting plasmid pSV2dhfr (available from the American Type Culture Collection or prepared according to the procedure of S. Subramani, et al., "Expression of the Mouse Dihydrofolate Reductase Complementary Deoxyribonucleic Acid in Simian Virus 40", Molecular and Cellular Biology 2:854–864 (September 1981) is digested with BamHI and EcoRI to yield the 5.0 Kb fragment (fragment 9) containing the ampicillin resistance gene, the SV40 origin, and the dhfr gene. The second portion of pSVCOW7 is obtained from plasmid p↑GH2R2 which is digested with the same restriction endonucleases used to cleave pSV2dhfr to obtain the

11)
GGATCCAAATCCGAGATGGAATACTGGAAGCACACCAATCACGGGAAAGATGCTGG

CCTAGGTTTAGGCTCTACCTTATGACCTTCGTGTGGTTAGTGCCCTTTCTACGACC

TAATGAGCTGGAAACATCCATGGCTACTCATGGC
ATTACTCGACCTTTGTAGGTACCGATGAGTACC

Oligonucleotide 11 will ligate to the HphI site and generate a BamHI restriction enzyme site on the 5' end of the cDNA fragment. Following ligation of oligonucleo- 2.1 Kb fragment (fragment 10) containing the 3' end of genomic bovine growth hormone gene, i.e., BGH gDNA. Plasmid pJGH2R2 is publicly available from an *E. coli* HB101 host, deposited with the Northern Regional Research Laboratories in Peoria, Ill. (NRRL B-15154). Fragments 9 and 10 are ligated to yield pSVCOW7 (7.1 Kb).

B. Construction of pGPFHN-IE-PA

The genes constructed in Examples 2-5 may be used for expression of a chimeric glycoprotein in CHO cells. The plasmid pGPFHN-1 will be used in the following example. The other chimeric genes are treated as described for pGPFHN-1 except when otherwise indicated. The assembly of pGPFHN-IE-PA is accomplished in two steps. First the gpFHN cDNA from pGPFHN1 is inserted into pSVCOW7 yielding pGPFHN-PA and then the immediate early promoter of cytomegalovirus is inserted to initiate transcription of the PIV3-like proteins yielding pGPFHN-IEPA.

STEP 1. Plasmid pSVCOW7 is cut with EcoRI and PuvII and fragment 11 (600 bp) containing the polyadenylation sequence of bovine growth hormone extending from the PvuII site in the 3' most exon of the BGH gene, to the EcoRI site downstream from the 3' end is isolated. For a complete discussion of the BGH polyadenylation sequence see the following references: (1) European patent application 01 12012, published on 27 Jun. 1984 wherein the identification and characterization of BGH genomic DNA is disclosed; (2) Woychik, R. P. et al., "Requirement for the 3' Flanking Region of the Bovine Growth Hormone Gene for Accurate Polyadenylation", Proc. Natl. Acad. Sci. USA 81:3944-3948 (July 1984); and, D. R. Higgs, et al., Nature 306:398-400 (24 Nov. 1983) and references cited therein disclosing that the nucleotide sequence AATAAA characterizes the polyadenylation signal at a location 11 to 30 nucleotides upstream (towards the 5' end) from the 3' end of the BGH gene.

A second sample of pSVCOW7 is cut with EcoRI and BamHI to yield fragment 12 (5.8 Kb). Fragment 12 can be alternatively derived from the EcoRI/BamHI fragment from parent plasmid pSV2dhfr available from Bethesda Research Laboratories. Fragment 12 contains the origin of replication from pBR322 and an ampicillin resistance gene expressed in *E. coli* which allows for the selection of the plasmid in *E. coli*. The fragment also contains the mouse dihydrofolate reductase cDNA in a construction that allows expression in mammalian cells. Subramani, et al., Mol. Cell. Biol. 1:854-864 (1981).

Plasmid pGPFHN1 is cut with BamHI and NruI to yield fragment 13 (2.7 Kb) which is gel isolated. The BamHI site is just upstream from the cDNA coding for the 5' untranslated sequences of the FHN MRNA, and the NruI site is a few bases downstream from the translation termination codon.

Fragments 11, 12 and 13 are ligated to form pGPFHN-PA (9.1 Kb) which is a replication vector capable of shuttling between *E. coli* and CHO cells. Plasmid pGPFHN-PA is transformed into *E. coli*.

STEP 2. In step 2, pGPFHN-PA is converted into expression plasmid pGPFHN-IE-PA by inserting the immediate early gene promoter from human cytomegalovirus (CMV I.E. promoter). The CMV I.E. promoter is obtained from the PstI digestion of the CMV genome. The restriction endonuclease cleavage maps of the region of the human cytomegalovirus (CMV) genome containing the major immediate early gene (CMV I.E.) have been described in detail Stinski, et al., J. Virol. 46:1-14, 1983; Stenberg, et al., J. Virol. 49:190-199, 1984; and, Thomsen, et al., Proc. Natl. Acad. Sci. USA, 81:659-663, 1984.

The Stinski and Thomsen references describe a 2.0 kilobase PstI fragment which contains the promoter for the major immediate early gene. When this 2.0 Kb PstI fragment is isolated and digested with Sau3AI, a 760 basepair fragment is obtained among the products. This 760 base pair fragment can be distinguished from the other products by its size and the presence of a SacI cleavage site and a BalI cleavage site within the fragment. Because of its convenient identification, utilization of this Sau3AI fragment is the preferred method of use of the CMV I.E. promoter as described in the present specification.

Plasmid pGPFHN-PA is cleaved with BamHI, and a Sau3AI fragment containing the CMV immediate early promoter is ligated into the compatible BamHI site. Plasmids containing the CMV promoter fragment in an orientation such that transcription from the promoter would synthesize an MRNA for a PIV3-like protein are identified by cleavage of the plasmids with SacI. The resulting plasmid is designated pGPFHN-IE-PA having the CMV I.E. promoter at the 5'-end of the cDNA and the BGH polyadenylation signal on its 3'-end. The plasmid is maintained in *E. coli* until transfection into CHO cells.

C. Transfection and Culturing of CHO Cells.

Plasmid pGPFHN-IE-PA is transfected into Chinese hamster ovary (CHO) cells deficient in dihydrofolate reductase(dhfr) using the calcium phosphate method for transfection of DNA into cells which is described in detail by Graham, et al., Introduction of Macromolecules into Viable Mammalian Cells, Alan R. Liss Inc., N.Y., 1980, pp. 3-25. The cell line used is the mutant DXB-11 originally available from L. Chasin, of Columbia University and completely described in Proc. Natl. Acad. Sci. USA 77:4216-4220 (1980). The above methods for transfection relies on the fact that cells which incorporate the transfected plasmids are no longer dhfr deficient and will grow in Dulbecco's modified Eagle's medium plus proline.

If the chimeric glycoprotein does not contain an anchor region, then supernatant from CHO cells expressing secreted chimeric FHN protein is clarified by low speed centrifugation. The supernatant is applied to a conconavalin A or lentil lectin column. The glycoprotein is eluted after extensive washing with a linear gradient of a $\alpha$-D-methylglucoside (0-0.5 M) in the above buffer. The eluted glycoprotein is dialyzed against PBS containing 0.1% Triton X-100 and applied to an affinity column. The affinity column is composed of either polyclonal or monoclonal antibodies directed against PIV3 linked to Sepharose 4B beads (Pharmacia, Piscataway, N.J.) by known techniques. The column is washed in dialysis buffer and the PIV3 FHN glycoprotein is eluted with PBS containing 0.1M glycine (pH 2.5) and 0.1% Triton X-100. The glycoprotein is dialyzed against saline and checked for purity by electrophoresis on a SDS-PAGE gel.

If the chimeric glycoprotein contains an anchor region, then the CHO cells expressing the glycoprotein are washed in phosphate buffered saline (PBS) and then lysed in PBS containing 1.0% Triton X-100 and 1.0% sodium deoxycholate. After pelleting the nuclei, the cytoplasmic extract is applied to a conconavalin A column and purified as described above for secreted glycoproteins.

Example 7 The Expression of PIV3 GPFHN Using Bovine Papilloma Virus (BPV)

A. The construction of a cloning vector containing a nontranscribable expression cassette suitable for replication in E. coli The constructions of pTFW8 and pTFW9 offer a convenient starting material for expressing PIV3 proteins using BPV. The transcription terminator of the deposited plasmid prevents the expression of PIV3 proteins and must be removed in a single step excision and ligation.

1. Construction of pTFW8

Plasmid pdBPV-MMTneo (342-12) described in Mol. and Cell Biol., Vol 3 (No. 11):2110–2115 (1983) and obtained from Peter Howley of the National Cancer Institute, Bethesda, Md., USA. Plasmid pdBPV-MMT neo (342-12) consists of three parts: a complete BPV-1 genome (100%) opened at the unique BamHI site; pML2 (a "poison-minus" derivative of pBR322); and a transcriptional cassette composed of the murine metallothionein I gene promoter, the neomycin phosphotransferase 11 gene of Tn5, and the simian virus 40 early-region transcriptional processing signals. Plasmid pdBPV-MMT neo (342-12) is first digested with BamHI to remove the BPV sequences which were isolated and stored for later insertion. The remaining fragment is religated using T4 ligase to form pMMpro.nptII (6.7 Kb). Removal of the BPV genome facilitates later genetic manipulations by creating unique restriction sites in the remaining plasmid. After the recombinations are complete, the BPV genome is replaced.

Plasmid pMMpro.nptII is digested with BglII and a synthetic DNA fragment 14 containing unique restriction sites is inserted and ligated using T4 ligase to yield pTFW8 (6.7 Kb). Plasmid pTFW8 is identical to pMMpro.nptII except for the insertion of unique restriction sites between the murine metallothionein I gene promoter and the neomycin resistance gene.

2. Construction of pTWF9

Plasmid pTWF9 contains the transcription terminator $T_I$ from phage lambda inserted between the metallothionein I gene promoter and the neomycin resistance gene. The transcription terminator can be obtained from Donald Court of the National Cancer Institute in Bethesda, Md. USA. The transcription terminator is supplied in pKG1800sib3 which is the same as pUS6 as described in Gene, 28:343–350 (1984), except that $t_I$ carries the sib3 mutation as described in Guarneros, et al., PNAS, 79:238–242 (1982). During the normal infection process of phage lambda, the $t_I$ terminator functions in the inhibition of bacteriophage ‡ int gene expression from $P_L$ and in the termination of int gene transcription originating from $P_I$. The terminator is excised from pKG1800sib3 using AluI and PvuI as fragment 15 (1.2 Kb), which is gel isolated and XhoI linkers are placed on either end of the fragment.

The linkers are available from New England Biolabs, Beverly, Ma., U.S.A. The terminator fragment bounded by XhoI complementary ends is then inserted into pTWF8 which has been previously digested with XhoI. The fragments are then ligated using T4 DNA ligase to yield pTWF9 (7.9 Kb). Plasmid pTWF9 was deposited in accordance with the Budapest Treaty. Plasmid pTFW9 is maintained in an E. coli host and has been deposited with the Northern Regional Research Center, Peoria, Ill., U.S.A. on Nov. 17, 1986 and assigned Accession Number NRRL B-18141.

B. The construction of pTFW/GPFHN

The genes constructed in Examples 2–5 may be used for expression of a chimeric glycoprotein using BPV. The plasmid pGPFHN-1 will be used in this example. The other chimeric genes are treated as described for pGPFHN-1 except when otherwise indicated. To construct pTFW/GPFHN, pGPFHN1 is digested with BamHI. Its ends are made flush with Klenow enzyme and synthetic BglII linkers (New England Biolabs) are ligated to the ends of the clone. The DNA is digested with BglII and designated fragment 16 (2.7 Kb). Fragment 16 containing the gpFHN gene (2.7 Kb) is then isolated from a gel. The purified fragment is ligated into pTFW9 which has been digested with BglII to yield pTFW/GPFHN (10.6 Kb).

C. Conversion of pTFW/GPFHN into a eukaryote expression vector

Plasmid pTFW/GPFHN is converted into a eukaryote expression vector by reinserting the 100% complete BPV-1 genome excised with BamHI. Plasmid pTFW/GPFHN is cut with BamHI and the BPV-1 intact genome, a 7.9 Kb fragment is inserted to yield pTFW/GPFHN/BPV* (18.5 Kb) which is replicated in E. coli until production of glycoprotein FHN by eukaryotic cells is desired.

D. Expression of gpFHN in murine C127 cells

Prior to transfection into murine C127 cells, pTFW/GPFHN/BPV* is digested with XhoI to excise the $T_1$ terminator and religated with T4 DNA ligase. The resulting plasmid pTFW/GPFHN/BPV (17.4 Kb) will now direct the expression of high levels of gpFHN which is secreted into the culture media. The C127 cells are available from the American Type Culture Collection and grown in Dulbecco's modified minimal essential media containing 10% fetal calf serum. The levels of gpFHN proteins in the media of the C127 cells are determined by Western blot experiments with anti-PIV3 antibody and 125$_I$-labeled protein A.

PIV3 gpFHN is purified from the culture media or cells as described in Example 6.

Example 8 The Expression of PIV3 GPFHN Using Baculovirus Virus

The following example relates to the expression of glycoprotein FHN in insect cell cultures. All procedures are detailed in Summers, M. D. and Smith, G. E., A Manual for Baculovirus Vectors and Insect Cell Culture Procedures published by the College of Agriculture, Texas Agricultural Experiment Station, Texas Agricultural Extension Service, College Station, Tex., 1986. The starting plasmid pAc373 (7.1 Kb) is a general baculovirus expression vector having a unique BamHI site immediately downstream from the polyhedron promoter for Autographs californica nuclear polyhedrosis virus (AcNPV). The polyhedron protein is a matrix protein that is nonessential for viral infection and replication in vitro. The 5plasmid is available from Professor Max Summers of the Department of Entomology, Texas A & M University, College Station, Tex. 77843 and is fully described in Molecular and Cell. Biology, 3(12):2156–2165 (1983).

A. Construction of pAcGPFHN

The genes constructed in Examples 2–6 may be used for expression of a chimeric glycoprotein using baculovirus. The plasmid pGPFHN1 will be used in this example. The other chimeric genes are treated as described for pGPFHN1 except when otherwise indicated. Plasmid pGPFHN1 is digested with BamHI and fragment 17 (2.7 Kb) containing the gpFHN gene is isolated from a gel. The purified fragment is ligated into pAc373 which has been digested with BamHI.

B. Transfection and culturing of S. Frugiperda

The gpFHN cDNA insert of pAcGPFHN is recombined with native AcNPV DNA by cotransfection in S. frugiperda. S. Frugiperda (SF9; ATCC CRL 171 1) are cultured in Grace Media (Gibco Lab. Livonia, Mich. 48150), 10% fetal calf serum and supplemented with Difco Lactalbumin hydrolysolate and yeastolate. The cells are cotransfected with AcNPV DNA and pAcGPFHN at 1 μg/ml and 2 μg/ml respectively. Resulting virus particles are obtained by collecting the media and removing cellular material by low speed centrifugation. The virus containing-media is then used to infect S. frugiperda. Subsequent infection of S. frugiperda using these viral particles which include both native viral DNA and DNA recombined with the cDNA coding for glycoprotein FHN will result in some cells expressing the PIV3 protein instead of the polyhedron protein. Purification of recombinant virus is accomplished by a series of limited dilution platings in 96-well tissue culture plates containing S. frugiperda cells. Wells containing recombinant virus are detected by dot blot hybridization using pGPFHN1 which has been labeled with $^{32}$p-dCTP by nick translation as a probe. Once sufficiently pure, the recombinant virus is detected by its unique occlusion-negative plaque morphology. PIV3 protein synthesized in recombinant baculovirus infected cells is detected by Western blot experiments with anti-PIV3 antibody and $^{125}$I-labeled protein A (Amersham Corp.).

The PIV3 protein is purified from the culture media or cells as described in Example 6.

Example 9 Preparation of a Vaccine

The immunogen can be prepared in vaccine dose form by well-known procedures. The vaccine can be administered intramuscularly, subcutaneously or intranasally. For parenteral administration, such as intramuscular injection, the immunogen may be combined with a suitable carrier, for example, it may be administered in water, saline or buffered vehicles with or without various adjuvants or immunomodulating agents such as aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Propionobacterium acnes), Bordetella pertussis, polyribonucleotides, sodium alginate, lanolin, lysolecithin, vitamin A, saponin, liposomes, levamisole, DEAE-dextran, blocked copolymers, ISCOMS or other synthetic adjuvants. Such adjuvants are available commercially from various sources, for example, Merck Adjuvant 65 (Merck and Company, Inc., Rahway, N.J.).

The proportion of immunogen and adjuvant can be varied over a broad range so long as both are present in effective amounts. For example, aluminum hydroxide can be present in an amount of about 0.5 % of the vaccine mixture ($Al_2O_3$ basis). On a per dose basis, the concentration of the immunogen can range from about 0.015 μg to about 1.5 mg per kilogram per patient body weight. A preferable dosage range is from about 0.5 μg/kg to about 0.15 mg/kg of patient body weight. A suitable dose size in humans is about 0.1–1 ml, preferably about 0.1 ml. Accordingly, a dose for intramuscular injection, for example, would comprise 0.1 ml containing immunogen in admixture with 0.5% aluminum hydroxide.

The vaccine can be administered to pregnant women or to women of child bearing age to stimulate maternal antibodies. The female can be revaccinated as needed. Infants can be vaccinated at 2 to 3 months of age after depletion of maternal antibodies and revaccinated as necessary, preferably at 6 to 9 months of age after maturation of the immune system. Babies born to unvaccinated mothers can be vaccinated at 2 to 3 months of age. The vaccine may also be useful in other susceptible populations such as elderly or infirmed patients.

The vaccine may also be combined with other vaccines for other diseases to produce multivalent vaccines. It may also be combined with other medicaments such as antibiotics.

CHART 1
CONSTRUCTION OF pGPF2

Plasmid pGPF1

```
                          PstI BstXI   NruI PstI
  *          |    |      |    |
  |        TTTFFFFFFFFFFFFFFFFTTT
           TcR
```

(a) Plasmid pGPF1 is digested with BstXI and NruI. Oligonucleotides 1 and 2 are ligated to the ends. The DNA is digested with BamHI and fragment 1 (1.6 Kb) is gel isolated.

Fragment 1
```
BamHI BstXI                  NruI BamHI
  |    |                      |    |
  1 1 1 1 1 FFFFFFFFFFFFFFFFFFFFFFF 2 2 2 2
```

(b) Plasmic pBR322 (4.4 Kb) is digested with BamHI and dephosphorylated with bacterial alkaline phosphatase. Fragment 1 is ligated into the BamHI site to form pGPF2 (6.0 Kb).

```
                    BamHI BstXI    NruI BamHI
  *                   |    |        |    |   *
  |                   1 1 1 1 FFFFFFFFFF 2 2 2
  AmpR
```

TcR = Tetracycline Resistance
AmpR = Ampicillin resistance
T = Guanosine/cytosine tail
F = Glycoprotein F
1 = Oligonucleotide 1
2 = Oligonucleotide 2

CHART 2
CONSTRUCTION OF A CHIMERIC FHN GLYCOPROTEIN GENE

Plasmid pGPHN1
```
                     PstI  DraI  PstI PstI
  *                   |    |      |    |   *
                      |
  TTTHHHHHHHHHHHHHHHHHHHHHHHTTT
                    TcR
```

(a) Plasmid pGPHN1 is digested with PstI. The ends are made blunt with T4 DNA polymerase and then dephosphorylated with bacterial alkaline phosphatase. An XbaI linker (linker 1) is ligated to the ends and fragment 2 (1.7 Kb) is gel purified.

-continued
CHART 2
CONSTRUCTION OF A CHIMERIC FHN GLYCOPROTEIN GENE

Fragment 2

```
                              DraI
                              |
  1 1 1 TTTHHHHHHHHHHHHHHHHHHHHH 1 1 1 1
```

(b) Fragment 2 is digested with DraI. An XbaI linker (linker 2) is ligated to the ends.
The DNA is digested with XbaI and Fragment 3 (1.3 Kb) is gel purified.

Fragment 3

```
     XbaI                              XbaI
     |                                 |
     2 2 2 HHHHHHHHHHHHHHHHHH 1 1 1
```

(c) Plasmid pGPF2 (Chart 1) is digested with XbaI and dephosphorylated with bacterial
alkaline phosphatase. Fragment 3 is ligated into the XbaI site to yield pGPFHN1.

```
                        BamHI   XbaI   XbaI BamHI
                        |       |      |    |
  |  FFFFFFFFFFHHHHHHHHH|FFFFF
     AmpR                Term
```

TcR = Tetracycline resistance
AmpR = Ampicillin resistance
T = Guanosine/cytosine tail
H = DNA sequences for HN glycoprotein
F = DNA sequences for F glycoprotein
1 = Linker 1
2 = Linker 2
Term = Translation termination signal CHART 3
Using Oligonucleotides to Generate FHN Genes
of Various Lengths (a) Oligonucleotide A consists of oligonucleotide 3 (57 bp), or
oligonucleotides 3 and 4 ligated together (117 bp), or
oligonucleotides 3, 4, and 5 ligated together (177 bp), or
oligonucleotides 3, 4, 5, and 6 ligated together (234 bp), or
oligonucleotides 3, 4, 5, 6, and 7 ligated together (290 bp).
Oligonucleotide B consists of oligonucleotide 8 (12 bp).
Oligonucleotides A and B are gel purified.

Oligonucleotide A          Oligonucleotide B 3333                       8888888

33334444

333344445555

3333444455556666

333344445555566667777

(b) Plasmid pGPHN1 is digested with PstI and DraI, and
Fragment 4 (1.3 Kb) is gel purified.

Fragment 4

```
     DraI         PstI
     |            |
     HHHHHHHHHHHHHHHH
```

(c) Oligonucleotides A and B are ligated to Fragment 4. The
DNA is digested with XbaI and fragment 5 is gel purified
(length of fragment 5 varies from 1330 bp to 1565 bp depending
on oligonucleotides contained within oligonucleotide A).

Fragment 5

```
     XbaI  DraI    PstI  XbaI
     |     |       |     |
     AAAAAHHHHHHHHHHHHHHHBBBB
```

(d) Plasmid pGPF2 is digested with XbaI and dephosphorylated
with bacterial alkaline phosphatase. Fragment 5 is then ligated into
the XbaI site of pGPF2 to form pGPFHN2.

Plasmid PGPFHN2

-continued
CHART 3
Using Oligonucleotides to Generate FHN Genes
of Various Lengths

```
              BamHI    XbaI    XbaI BamHI
              |        |       |    |
         |  FFFFFFFFFFAAAHHHHHBBFFFF
         AmpR                   |
                                Term
```

AmpR = Ampicillin resistance
F = DNA sequences for F glycoprotein
H = DNA sequences for HN glycoprotein
A = Oligonucleotide A
B = Oligonucleotide B
Term = Translational termination signal CHART 4
Construction of an FHN Gene Containing an Anchor Region Plasmid pGPHN1

```
                PstI DraI    PstI PstI
                |    |       |    |
     |  TTTTTHHHHHHHHHHHHHHHHHTTTTT
     TcR
```

(a) Plasmid p GPHN1 is digested with DraI and PstI.
Oligonucleotide 9 is ligated to the DNA, then Oligonucleotide 10
is ligated to the DNA. The DNA is digested with XbaI and
fragment 6 (1.3 Kb) is gel purified.

Fragment 6

```
     XbaI DraI    PstI    XbaI
     |    |       |       |
     9 9 9 HHHHHHHHHHHHHH 10 10 10
```

(b) Plasmid pGPF2 is digested with XbaI and dephosphorylated
with bacterial alkaline phosphatase. Fragment 6 is ligated into the
XbaI site of pGPF2 to form pGPFHN3.

Plasmid pGPFHN3

```
            BamHI XbaI DraI    PstI XbaI BamHI
            |     |    |       |    |    |
     |  FFFFFFFF 9 9 HHHHHHHH 10 10 AAAA |
        AmpR                              Term
```

TcR = Tetracycline resistance

CHART 4
Construction of an FHN Gene Containing an Anchor Region

AmpR = Ampicillin resistance
T = Guanidine/Cytosine tail
F = DNA sequences for F glycoprotein
H = DNA sequences for HN glycoprotein
9 = Oligonucleotide 9
10 = Oligonucleotide 10
Term = Translational Termination Signal
A = DNA sequences coding for anchor region of F glycoprotein

CHART 5
Preparation of HN Gene for Construction of HNF Chimeric Gene

Plasmid pGPHN1

```
              PstI  HphI    PstI PstI
  *            |    |        |    *
   |————————————————————————————————
   T  TTHHHHHHHHHHHHHHHHHHHHHHTTT
  TcR
```

(a) Plasmid pGPHn1 is digested with HphI. Oligonucleotide 11 is ligated to the DNA. The DNA is digested with BamHI and PstI, and fragment 7 (1.7 Kb) is gel purified.

Fragment 7

```
   BamHI HphI       PstI
    |     |          |
    ———————————————————
    11 11 11 HHHHHHHHHHHH
```

(b) Plasmid pUC19 is digested with BamHI and PstI. Fragment 7 is ligated into pUC19 to form pGPHN2.

Plasmid pGPHN2

```
             BamHI HphI    PstI
  *           |    |        *
   |——————————————————————————
   T            11 11 11 HHHHHHHHHHHH
  AmpR
```

T = Guanosine/Cytosine tail
TcR = Tetracycline resistance
AmpR = Ampicillin resistance
H = DNA sequences for HN glycoprotein
11 = Oligonucleotide 11

CHART 6
Insertion of F cDNA into pGPHN2

Plasmid pGPF1

```
              PstI BstEII   XbaI PstI
  *            |    |        |    *
   |————————————————————————————————
   T   TTFFFFFFFFFFFFFFFFFFFFFFFTTT
  TcR
```

(a) Plasmid pGPF1 is digested with BstEII and XbaI. Oligonucleotides 12 and 13 are ligated to the DNA. The DNA is digested with PstI and fragment 8 (1.2 Kb) is gel purified.

Fragment 8

CHART 6 (continued)
Insertion of F cDNA into pGPHN2

```
   PstI BstEII     XbaI    PstI
    |    |          |       |
    ——————————————————————————
    12 12 FFFFFFFFFFFFFF 13 13
```

(b) Plasmid pGPHN2 (Chart 5) is digested with PstI. Fragment 8 is ligated into the PstI site of pGPHN2 to form pGPHNF1.

Plasmid pGPHNF1

```
         BamHI HphI  PstI   BstEII  XbaI  PstI
  *       |    |      |      |      |      *
   |————————————————————————————————————————
   T   11 11 HHHHHHHH 12 12 FFFFFFFF 13 |13
  AmpR                             Term
```

AmpR = Ampicillin resistance
TcR = Tetracycline resistance
T = Guanosine/Cytosine tail
F = DNA sequences for F glycoprotein
H = DNA sequences for HN glycoprotein
11 = Oligonucleotide 11
12 = Oligonucleotide 12
13 = Oligonucleotide 13
Term = Translational Termination Signal

I claim:

1. An expression system comprising a suitable host containing a DNA sequence capable of expressing a chimeric glycoprotein consisting essentially of the extracellular domain of parainfluenza virus type 3F protein linked to the extracellular domain of parainfluenza virus type 3 HN protein.

2. The expression system according to claim 1 wherein said suitable host is selected from group consisting of yeast cells, mammalian cells and insect cells.

3. The expression system according to claim 2 wherein said suitable host is selected from the group consisting of Chinese hamster ovary cells, murine C127 cells and S. Frugipersa cells.

4. The expression system according to claim 1 wherein said suitable host secretes said chimeric glycoprotein.

5. The expression system according to claim 1 wherein said DNA sequence is contained in a plasmid.

6. The expression system according to claim 5 wherein said plasmid is under the control of a cytomegalovirus promoter.

7. The expression system according to claim 5 wherein the replication of said plasmid while in a suitable eukaryote host is under the control of bovine papilloma virus DNA sequences.

8. The expression system according to claim 1 wherein said DNA sequence is contained in a recombinant virus of the baculovirus family.

9. The expression system according to claim 8 wherein the virus is Autographs californica nuclear polyhedrosis virus.

* * * * *